United States Patent
Jansen et al.

(10) Patent No.: US 11,105,725 B2
(45) Date of Patent: Aug. 31, 2021

(54) COMPUTER-IMPLEMENTED METHOD OF ANALYZING DATA FROM MEASURED VALUES OF CHARACTERISTICS OF OBJECTS IN SAMPLES

(71) Applicants: STICHTING RADBOUD UNIVERSITEIT, Nijmegen (NL); UMC UTRECHT HOLDING B.V., Utrecht (NL)

(72) Inventors: Jeroen Jansen, Nijmegen (NL); Lutgarde Buydens, Nijmegen (NL); Leo Koenderman, Utrecht (NL); Bart Hilvering, Utrecht (NL); Oscar Van Den Brink, Utrecht (NL)

(73) Assignees: STICHTING RADBOUD UNIVERSITEIT, Nijmegen (NL); UMC UTRECHT HOLDING B.V., Utrecht (NL)

( * ) Notice: Subject to any disclaimer, the term of this patent is extended or adjusted under 35 U.S.C. 154(b) by 471 days.

(21) Appl. No.: 15/106,064

(22) PCT Filed: Dec. 18, 2014

(86) PCT No.: PCT/NL2014/050885
§ 371 (c)(1),
(2) Date: Jun. 17, 2016

(87) PCT Pub. No.: WO2015/093958
PCT Pub. Date: Jun. 25, 2015

(65) Prior Publication Data
US 2017/0003212 A1    Jan. 5, 2017

(30) Foreign Application Priority Data

Dec. 18, 2013 (NL) ..................... 1040550
Jun. 29, 2014 (NL) ..................... 1040872

(51) Int. Cl.
| | | |
|---|---|---|
| *G01N 33/48* | (2006.01) | |
| *G01N 33/50* | (2006.01) | |
| *G01N 15/10* | (2006.01) | |
| *G01N 15/14* | (2006.01) | |
| *G06K 9/62* | (2006.01) | |
| *G06K 9/00* | (2006.01) | |
| *G16B 15/00* | (2019.01) | |
| *G16H 50/20* | (2018.01) | |

(52) U.S. Cl.
CPC ......... *G01N 15/10* (2013.01); *G01N 15/1429* (2013.01); *G06K 9/0014* (2013.01); *G06K 9/6247* (2013.01); *G16B 15/00* (2019.02); *G01N 2015/1006* (2013.01); *G01N 2015/1402* (2013.01); *G16H 50/20* (2018.01)

(58) Field of Classification Search
CPC ............... G01N 15/10; G01N 15/1429; G01N 2015/1006; G01N 2015/1402; G06K 9/6247; G06K 9/0014; G16B 15/00; G16H 50/20
See application file for complete search history.

(56) References Cited

U.S. PATENT DOCUMENTS

2012/0214190 A1* 8/2012 Hou ................. G01N 33/56972
435/29

OTHER PUBLICATIONS

Wold. Pattern recognition by means of disjoint principal component models. Pattern Recognition, vol. 8, pp. 127-139. (Year: 1976).*
Laerum et al. Clinical application of flow cytometry: a review. Cytometry, vol. 2, pp. 1-13. (Year: 1981).*

* cited by examiner

Primary Examiner — Russell S Negin
(74) Attorney, Agent, or Firm — Nixon & Vanderhye, P.C.

(57) ABSTRACT

The invention relates to a computer implemented method of analysing data comprising measured values of characteristics of objects in samples, the data comprising —a first set of data ($X_{ireference}$)' with measured values of characteristics of objects in reference samples; —a test set of data ($X_{itest}$) with measured values of the characteristics of objects in a test sample; characterised by the method comprising; —fitting a control model to the first set of data to determine control loadings ($P_{control}$) each representing an independent correlation between characteristics; —projecting the first set of data ($X_{ireference}$) onto the control loadings ($P_{control}$) for determining a first set control scores ($T_{control,ireference}$) and determining one or more confidence intervals for the first set of control scores ($T_{control,ireference}$); —projecting the test data onto the control loadings ($P_{control}$) for determining test control scores; —determining if the test control scores are within one or more the confidence intervals.

15 Claims, 1 Drawing Sheet

COMPUTER-IMPLEMENTED METHOD OF ANALYZING DATA FROM MEASURED VALUES OF CHARACTERISTICS OF OBJECTS IN SAMPLES

RELATED APPLICATIONS

This application is the U.S. national phase of International Application No. PCT/NL2014/050885 filed 18 Dec. 2014 which designated the U.S. and claims priority to NL 1040550 filed 18 Dec. 2013 and NL 1040872 filed 29 Jun. 2014, the entire contents of each of which applications are hereby incorporated by reference.

The invention relates to a method of analysing data, a computer program, a computer readable medium and a data analysis system In a method known from WO2012/048906 of analysing data from a cytometer the data comprises data from healthy individuals and challenged individuals.

In this method, the data from healthy individuals and challenged individuals is individually represented in matrix form. In combination the number of healthy individuals and the perturbed individuals is represented as I, the index for an individual is i. The data comprises measured values for J characteristics of cells. For individual i, there are measured values for $N_i$ cells, the data for each cell of an individual having an index $n_i$.

A model is fitted to the data, thereby determining a two model loadings using principal component analysis (PCA), i.e. only 2 components are used.

Then the data of all individuals is projected onto the model loadings and represented in a scatterplot wherein the two orthogonal axes correspond to the two model loadings. Two scores per cell are determined during projection of data of all individuals. Each cell is indicated as a dot in the scatterplot. The coordinates of the dots correspond to the scores. For the challenged individuals the dots are identified in the scatterplot and one or more gates are determined in the scatterplot. A gate here is an area in the scatterplot.

In practice, data from a cytometer usually corresponds to 1000 objects per sample.

Because of the complexity of the calculations, performing the principal component analysis by hand is only possible for around 2 objects.

In practice increased sensitivity for determining presence of an illness is desired as long as this can be obtained using a computer as well as increased sensitivity for determining the exact illness when using a computer. For determining the presence of an illnesses it is necessary to analyse data from large numbers of objects and because of this large number, it is desired to be able to determine the illnesses using a computer so that the presence of the illness is established before the health of the patent worsens or before the patient recovers or at least while the illness of the patient does not change too much. Moreover, such data is comprised on a computer readable medium. In addition, it is desired to be able to determine the presence of an illness automatically, to avoid subjective influence and differences between operators or laboratories. Furthermore, gating scores is a subjective activity and may lead to variations depending on the person or laboratory carrying out the gating and an automatic way to gate objects is desired.

An objective technical problem therefore is to provide a method with increased sensitivity for determining presence of an illness using a computer. It is an object of the invention to provide a method that at least partially solves these problems.

According to first embodiment of the invention this object is reached by the computer implemented method of claim 1.

It will be appreciated by the person skilled in the art that data comprising measured values of characteristics of objects in samples may relate to data from a cytometer (the computer implemented method then being a cytometric method) and may relate to the measured quantities of radiation (such as light) whereby for a single sample several objects (such as cells or particles) are fed along a measurement station that emits measurement radiation. The measured quantity of radiation for instance corresponds to the presence of a substance in the objects. This correspondence may be established by the presence of markers that bind to the substance in the objects and that are sensitive to the measurement radiation in that they scatter or diffract the measurement radiation or absorb it. The absorption may lead to a fluorescent or phosphorescent decay, which may be measured or the absorption may be measured. The cytometer may be a flow cytometer. The cytometer may be a mass cytometer. The cytometer may be arranged to measure objects marked with mass labels, for instance isotopically.

The characteristics of the objects may change for instance as a perturbation to a challenge, such as an LPS challenge to cells of individuals, as perturbation to a disease, ageing periodically (for instance in a night-day rhythm). The characteristics may also change under the influence of pollution.

The test set of data does not overlap with the first set of data.

The reference samples are obtained from individuals that are not subjected to a challenge or diseased. Because the control model is fitted to only the data of the reference samples, the control loadings do not represent correlations (relations) between characteristics present only in perturbed samples, i.e. samples for which it is established that they do not correspond to a reference situation. In other words, perturbed samples are samples the method is arranged to discriminate from the reference samples.

For determining if there is a deviation from the reference samples, it suffices to be able to discriminate from healthy samples and it is not necessary to be able to also find what the deviation encompasses. Therefore, although finding correlations (relations) between characteristics that are present only in perturbed samples and not in reference samples may be useful, finding such correlations between characteristics that are present only in perturbed samples is unnecessary for an efficient method with the purpose to only discriminate between perturbed samples and reference samples. A lower number of dimensions suffices in the method according to the embodiment and the confidence intervals have sharper borders when only representing correlations between characteristics present only in reference samples compared to in the same determination of control loadings also representing other correlations. Put differently, for the same number of dimensions (components or loadings) the control model determined by the method of this embodiment is better suited to describe the data of reference samples than the model determined by method of the prior art. In addition, the use of confidence intervals makes the method objective.

In an advantageous further embodiment, individual objects in the test data set for which the test control scores are outside the one or more confidence intervals are separated from the other objects in the test sample. This separation may be conducted by a sorter such as a sorter in a cytometer, such as a flow cytometer.

According to a second embodiment of the invention, there is provided a computer implemented method according to claim 2.

A principal component analysis is an efficient way to determine the control loadings. In an advantageous embodiment, the number of dimensions, i.e the number of principal components, is determined using a scree plot or cross-validation.

According to a third embodiment of the invention, there is provided a computer implemented method according to claim 3.

The inventors realised that centering to the average value of the measurements of each sample, i.e. of each individual may be applied after evaluating the absence of systematic difference between profiles of the measured characteristics of objects in reference and perturbed samples.

To check this, such an evaluation was conducted by comparing average profiles of measured characteristics of objects with an object weighted principal component analysis model. In the object weighted principal component analysis model the averages per sample were weighted according to the number of objects they represent. The scores of this object weighted principal component model indicated that there was no such systematic offset and therefore sample centering does not remove information of relevance from the data.

By centering the data per sample, the first set of control scores describes the variation of the characteristics per sample. This means that the mutual variation within the first set of control scores may be compared between samples. The one or more confidence interval can therefore be determined for samples and for groups of samples so that it is possible to determine for samples if they are reference or perturbed, when compared to the confidence interval of all reference samples.

According to a fourth embodiment of the invention, there is provided a computer implemented method according to claim 4.

Centering the test set of data results in the test set of control scores describing the variation of the characteristics per sample.

According to a fifth embodiment of the invention, there is provided a computer implemented method according to claim 5.

By determining at least two principal control loadings, a two-dimensional graphical representation such as a biplot can be used to analyse the results for all independent correlations for a combination of two of the principal control loadings of the at least two principal control loadings. By determining if the test control scores along the vector are within the one or more confidence intervals, it is established if the characteristic is present in equal variability as normal within reference samples or more or less variably present than normal within reference samples. Combined with separately gathered information linking variability in a characteristic to a perturbation, this provides a way to determine if a sample is exposed to a specific perturbation, such as a disease. By determining more than two principal components, the two-dimensional biplot can be used to represent combinations of two out of the total number of selected principal components.

According to a sixth embodiment of the invention, there is provided a computer implemented method according to claim 6.

This embodiment increases the selectivity of the method with regard to information related to the perturbation. This is accomplished by additional modelling for relations between characteristics that are not exhibited by reference samples but that are exhibited by perturbed samples. The modelling for the relations between characteristics that are exhibited by reference samples (and that also may be exhibited by perturbed samples) is not affected, as the control model is based on data from the first set of data only and not also on data from the second set of data, i.e. the control loadings are determined based on data from the first set of data, the reference samples, only.

The perturbation loadings correspond to components determined in the further principal component analysis.

In an advantageous embodiment, the first set of control residuals is determined while projecting the first data onto the control loadings in the step for determining a first set of control scores.

In an advantageous embodiment, the test set of control residuals is determined while projecting the test set of data onto the control loadings for determining test control scores. The test sets of control residuals obtained from several perturbed samples are then described by a further principal component analysis.

In an advantageous further embodiment, individual objects in the test data set for which the test control scores are outside the one or more further confidence intervals are separated from the other objects in the test sample. This separation may be conducted by a sorter such as a sorter in a cytometer, such as a flow cytometer.

According to a seventh embodiment of the invention, there is provided a computer implemented method according to claim 7.

A principal component analysis is an efficient way to determine the perturbed loadings. In an advantageous embodiment, the number of dimensions, i.e. the number of principal components, is determined using a scree plot or cross-validation.

According to an eighth embodiment of the invention, there is provided a computer implemented method according to claim 8.

Where the test set of data is the second set of data, the method is advantageous for research purposes. The method according to this embodiment may for instance be used to investigate if certain perturbations (such diseases) can be detected according the method or if other characteristics need to be measured.

According to a ninth embodiment of the invention, there is provided a computer implemented method according to claim 9.

As the second set of data is the test set of data, data corresponding to test scores falling within the one or more confidence intervals corresponds to data in the second set of data. Removing this data from the second set of data contributes to fitting the perturbation model to relevant data only and increases the sensitivity to finding correlations between characteristics that are not present within the reference set of data.

According to a tenth embodiment of the invention, there is provided a computer implemented method according to claim 10.

As the perturbation model models for correlations that are not within the control model, a confidence interval for those correlations can be used advantageously to identify if objects in test samples comply with the perturbations captured in the second set of data or relate to another perturbation.

For instance, of a sample of which the status is unknown, it may be determined that it is perturbed, but not according to the known perturbations, i.e. the perturbations captured in the second set of data. In this case it would be perturbed according to an unknown perturbation.

According to an eleventh embodiment of the invention, there is provided a computer implemented method according to claim 11.

The further principal component analysis is the principal component analysis used to determine the perturbation loadings and as such can be used to select two principal perturbation loadings. By selecting only two principal perturbation loadings, the method of the eleventh embodiment provides a way to graphically interpret the data in a highly sensitive manner with respect to a perturbation.

According to a twelfth embodiment, the invention further provides for a method for analysing data according to claim 12.

A cytometer can be used to measure various characteristics of cells of particles.

In an advantageous embodiment, the objects are cells or particles.

According to a thirteenth embodiment, the invention further provides for a computer program according to claim 13.

According to a fourteenth embodiment, the invention further provides for a computer readable medium according to claim 14.

The computer readable medium may for instance be a floppy, a hard disk, a USB-stick, a SSD-drive.

According to a fifteenth embodiment, the invention further provides for a data analysis system according to claim 15.

The data analysis system may be a computer receiving the data from a cytometer, such as a flow cytometer. The data analysis system may also be part of a cytometer, such as a multicolour flow cytometer.

The data analysis system provides the advantages of the computer implemented method of any of the claims 1 to 11.

The data analysis system may comprise
input means to receive a first set of data with measured values of characteristics of objects of reference samples;
input means to receive a second set of data with measured values of the characteristics of objects of perturbed samples;
input means to receive a test set of data with measured values of the characteristics of objects of a test sample.

According to a sixteenth embodiment, the invention further provides for a cytometer according to claim 16.

Cytometric measurements typically relate to order of magnitude 1000 objects per sample. By using a computer, the According to a seventeenth embodiment, the invention further provides for a cytometer according to claim 17.

By checking if the test control scores that correspond with the objects are inside the one or more confidence intervals, there is an objective measure to separate the objects.

As the cytometer uses a computer implemented method, the separation can be done fast and possibly even real time: i.e. whenever the characteristics of an object are measured, the object can be diverted into separate directions based on the check of the corresponding test control scores.

Examples of embodiments of the invention will now be described with reference to the accompanying schematic drawing. The schematic drawing is not necessarily to scale and certain features may be exaggerated to better illustrate and explain the present invention. Further, the examples are not intended to be exhaustive or otherwise limit or restrict the invention to the precise configurations shown in the drawings and disclosed in the following detailed description.

In the description of the examples, loadings correspond to components determined in a principal component analysis. Scores refer to the expression on the components (loadings) and may be seen as coefficients in the linear model wherein the components are variables. This applies to the control model and control loadings as well as to the perturbation model and perturbation loadings.

In a first example of the computer implemented method according to the invention there is a data set of measured values for characteristics of objects in different samples. The measured values here correspond to the abundance of the presence of surface markers. The samples are either reference samples (such reference samples are indicated as $1_{reference} \cdots i_{reference} \cdots I_{reference}$) or perturbed samples. In this example the samples relate to cytometric measurements on cells from individuals stored in a memory of the cytometer. Each sample is taken from a unique individual. The reference samples are from healthy individuals. The perturbed samples are from individuals which are challenged with lipopolysaccharide (LPS). Such perturbed samples are indicated as $1_{perturbed} \cdots i_{perturbed} \cdots I_{perturbed}$.

The data set comprises data obtained by a multicolour flow cytometer. The data is stored in a memory of the cytometer.

A modelling step of the method describes the surface marker variability between objects of reference samples, leading to a control model described as $$S_{control}^{-1}(X_{i_{reference}} - 1_{Ni_{reference}} m_{i_{reference}}^T) = T_{control,i_{reference}} P_{control} + Y_{i_{healthy}} \quad (1)$$

wherein $S_{control}^{-1}$ is a diagonal matrix of size J that contains the standard deviation of each surface marker among all objects within reference samples, vector $m_{i_{reference}}$ of length J contains the average surface marker expression of all objects in sample $i_{reference}$ and performs the sample centering of the data.

After fitting the data to the model with computation means of a computer, the matrix $T_{control,i_{reference}}$ of dimensions $(N_{i_{reference}} \times R_{control})$ contains control scores of sample $i_{reference}$ The matrices $T_{control,i_{reference}}$ for all reference samples together form a first set of control scores.

$P_{control}$ Is a matrix $(J \times R_{control})$ representing the control loadings.

$Y_{i_{reference}}$ Represents the residuals of this control model for each sample; for all samples combined they are referred to as a first set of control residuals. $1_{control} \cdots r_{control} \cdots R_{control}$ Indicate the components of the control model.

The control scores, the control loadings and the residuals are computed using computation means of a computer which reads the first set of data from a computer readable medium.

The variability in the surface marker-profile $X_{i_{reference}}$ of each reference sample is expressed by the first control scores $(T_{control,i_{reference}})$. The first control scores $(T_{control,i_{reference}})$ for all the reference samples together form a first set of control scores.

These first control scores $(T_{control,i_{reference}})$ and control loadings (columns in matrix $P_{control}$) are different from the PCA scores and loadings of the prior art, because the control model is fitted on the reference samples alone. The method strives to discriminate with respect to the reference samples. This difference with the prior art is also reflected in the control loadings $P_{control}$ determined according to the example according to the invention. The control loadings $P_{control}$ exclusively describe relationships (correlations) between surface markers exhibited by reference samples. However the control loadings $P_{control}$ do not explicitly exclude relations (correlations) in perturbed samples if they are also exhibited by reference samples $i_{reference}$.

One model aspect that is not explicit in equation (1) is that the control model is fitted such, that each sample $i_{reference}$ may contribute an equal amount of information to the control model. The method thereby averages between all samples $i_{reference}$ rather than between all objects. This is done by weighing the model with the sample object count $N_{i_{reference}}$ as indicated in step 2a of the algorithm below.

The control model employs sample-based centering, which centers the surface marker profiles in the first set of data ($X_{i_{reference}}$) on the average surface marker expression of each reference sample. This modelling choice results in ($T_{control, i_{reference}}$) describing the surface marker variability per sample, which means that instead of directly comparing the absolute score values between samples, their mutual variability may be compared. This choice results from consistent 'offset' differences between surface marker intensities that are empirically observed, that are not related to the perturbation and therefore distract from the variability between objects within the same sample that is of primary interest. Instead of the variability among all measured objects as in the prior art, the surface marker profiles are scaled here with the standard deviation ($S_{control}$) among all objects of reference samples. The control model therefore fits the information in reference samples exclusively.

The sample-based centering is used throughout the method as can be seen in the algorithm below.

As a result of fitting the control model to data from the reference samples and not to perturbed samples, the control loadings do not fit all relations between the surface markers that are related to LPS perturbation. How the control model then describes the surface marker profiles of perturbed samples can be found from their orthogonal projection onto the control loadings as a step in the method. This orthogonal projection then leads to the model of perturbed samples in a second set of data according to the following equation (2):

$$S_{control}^{-1}(X_{i_{perturbed}} - 1_{N_{i_{perturbed}}} m_{i_{perturbed}}^T) = T_{TC, i_{perturbed}} P_{control}^T + Y_{i_{perturbed}} \quad (2)$$

where $T_{TC, i_{perturbed}}$ of dimensions ($N_{i_{perturbed}} \times R_{control}$) represents the scores of a perturbed sample expressed on the control loadings and $Y_{i_{perturbed}}$ represents the residuals of the projection. The second set of data is fitted to the model using computation means of a computer which retrieves the second set of data from a computer readable medium. For all perturbed samples combined, these $Y_{i_{perturbed}}$ are referred to as a second set of control residuals.

The scores $T_{TC, i_{perturbed}}$ that result from this projection describe the variability among sample objects in perturbed samples expressed on the relations between surface markers exhibited by reference samples. The surface marker intensities have been scaled with the same parameters in $S_{control}$, such that the variability between sample objects in the control model can be compared between reference samples $I_{reference}$ and perturbed samples.

The scores of perturbed samples may be compared to those from reference samples $i_{reference}$ obtained from equation (1), which may reveal how the perturbation, in this example the challenge with LPS, alters the variability among objects within the same sample through the specific combinations between surface markers exhibited by reference samples. Disruptions in these relationships may be identified on the basis of the scores per sample.

The use of a second set of data is however optional.

In practice the method may be used for testing test samples for whom it is unknown if the sample is perturbed or reference and if perturbed by what perturbation. For the test sample a test set of data is obtained by cytometric measurements. The test set of data is projected onto the control loadings, thereby determining test control scores (after scaling and sample centering analogue to what was described for the first set of data).

Figure 1:
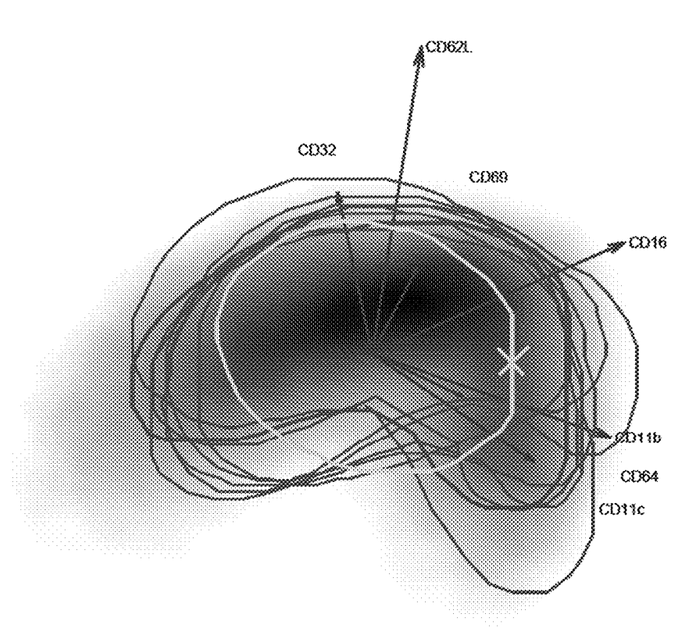
The FIGURE illustrates a biplot of a typical LPS perturbed sample with respect to the control loadings, together with a confidence interval that indicates the variability between objects observed in reference samples, as expressed on the control loadings.

The scores of a test sample, may be presented graphically. For this a biplot is produced using an output means, such as a printer or a display, of the computer, such as biplot illustrated in the FIGURE. In the biplot, a typical LPS-perturbed sample is shown based on a projection on the control loadings. White areas indicate high object densities. The arrows represent vectors. The length of the vectors represents the amount of surface marker variability into a certain direction. The direction relates to a specific surface marker. For each vector the specific surface marker is indicated in the biplot. The closed loop line marked by an "x" represents a confidence interval based on the complete first data set. Here the second set of data is used as well and the other closed loop lines indicate perturbed confidence intervals for LPS perturbed samples, which means here that for each of these closed loop lines a percentage of the objects has control scores within the perturbed confidence interval. The confidence intervals (i.e. the confidence intervals based on the complete first data set as well as the perturbed confidence intervals) may for instance be 80% confidence intervals, or 95% confidence intervals.

By checking for a sample, such as the test sample, if its perturbed confidence interval has an area outside the confidence interval based on the complete first data set in the direction of a vector, it can be determined if the hypothesis that that sample corresponds to the reference can be rejected. If so, it can be concluded that the sample obtained from the test person contains objects of which the correlation between the characteristics is not found in reference samples, and that therefore the test sample is perturbed, i.e. it is to be discriminated from the reference. Checking the position of the perturbed confidence interval with respect to the confidence interval based on the complete first data set may be conducted automatically, i.e. without producing a biplot.

This can be conducted automatically, as they can be determined based on pre-determined values such as the desired degree of confidence or the number of objects of an individual that have a score that lies outside the confidence interval determined on the first data set.

Objects (here cells) having scores outside the confidence interval may be identified using a comparator of the computer and separated from the other objects in a sample by a sorter. Sorters are well known for flow cytometers.

Such objects may also be used to compose a new second set of data from the test set of data wherein the second set of data does not comprise any objects that comply with the reference samples.

Independent of the composition of the second set of data however, the control model does not model for relationships between surface markers not exhibited by reference samples. This implies that there will be a considerable systematic mis-fit of the perturbed surface marker profiles on the control loadings that will correspond to such perturbation-specific processes. This information will end up in the projection residuals $Y_{i_{perturbed}}$, which may be subsequently explored in a further step of the approach. In the further step a perturbation model is used according to equation (3). The perturbation model is fitted using a further principal component analysis that fits this systematic information related to relationships that do not occur in reference circumstances.

$$Y_{i_{perturbed}} = T_{perturbation,i_{perturbed}} P_{perturbation}^T + E_{i_{perturbed}} \quad (3)$$

Here matrix $T_{perturbation,i_{perturbed}}$ ($N_{i_{perturbed}} \times R_{perturbation}$) represents object scores of samples $i_{perturbed}$ (perturbation scores) and matrix $P_{perturbation}$ ($J \times R_{perturbation}$) represents the corresponding loadings on principal components $1 \ldots r_{perturbation} \ldots R_{perturbation}$;

$E_{i_{perturbed}}$ represents perturbation model residuals. The residuals are not expected to contain any systematic information regarding the perturbation.

The perturbation scores, the perturbation loadings and the perturbation residuals are computed using computation means.

The scores $T_{perturbation,i_{perturbed}}$ contain the object variability in surface markers after the LPS perturbation, obtained without prior biological assumptions and the corresponding loadings $P_{perturbation}$ contain the relations among surface markers that occur in perturbed, but not in reference samples and are therefore perturbation-specific. Together the scores of the second set of data in the control model and of their residuals in the perturbation model form an individualised perturbation surface marker-profile that can be compared between perturbed samples: also the perturbation scores and perturbation loadings from equation (3) can be represented in a bi-plot (a single two-dimensional figure) if $R_{perturbation}$ is two, i.e. if the further principal component analysis results in two principal perturbation components. If more than two principal components are selected for the further principal component analysis, the bi-plot can be used to describe combinations of two out of the selected principal components.

When the number of principal components ($R_{control}$) is chosen too low during the principal component analysis, systematic information shared by reference and perturbed samples ends up in ($Y_{i_{perturbed}}$), as it is not part of the orthogonal projection in equation (2) and therefore also becomes part of the scores ($T_{perturbation,i_{perturbed}}$) through equation (3). Therefore, the scores ($T_{perturbation,i_{perturbed}}$) of the second set of data in the perturbation model as determined in equation (3) and their spread within perturbed samples can be quantitatively evaluated against a benchmark of spread that would be present in control samples, which here are the reference samples. This benchmark is determined by an orthogonal projection of the control model residuals of the reference samples ($Y_{i_{healthy}}$, from equation (1)) onto the perturbation loadings from equation (3), leading to another step in the example of the method according to the invention given in equation (4).

$$Y_{i_{reference}} = T_{CT,i_{reference}} P_{perturbation}^T + E_{i_{reference}} \quad (4)$$

where $T_{CT,i_{reference}}$ of dimensions ($N_{i_{reference}} \times R_{perturbation}$) represents a first set of perturbation scores.

$E_{i_{reference}}$ represents residuals.

The calculation of the first set of perturbation scores $T_{CT,i_{reference}}$, the residuals $E_{i_{reference}}$ and the perturbation loadings is carried out by calculation means.

The first set of perturbation scores $T_{CT,i_{reference}}$ will not individually be of biomedical interest. The first set of perturbation scores $T_{CT,i_{reference}}$ is not supposed to individually contain relevant information because the relevant information is modelled in the control model. However, the perturbation scores in the first set of perturbation scores $T_{CT,i_{reference}}$ have a more validatory function. The first set of perturbation scores $T_{CT,i_{reference}}$ for all reference samples may be used to determine a confidence interval. The objects of a perturbed sample that fall inside this interval do not vary more from the average $m_{i_{perturbed}}^T$ than could be expected from the variability between objects in reference samples. The objects that exceed this interval are therefore of primary interest to the LPS perturbation as they exceed this expected variability. Such objects are found by using a comparator of the computer to compare the scores of the objects in the perturbed sample that fall outside the confidence interval.

The validity of the sample centering (this is done if there is no systematic difference between the surface marker profiles of reference and perturbed samples) can optionally be evaluated by comparing the average surface marker profiles with an object weighted PCA model, in which the averages per sample are weighted according to the number of objects they represent. In a test, the scores of this object weighted PCA model indicated that there is no such systematic offset, such that sample centering does not remove information of biomedical relevance, i.e. differences in the average expression of surface markers between reference and perturbed samples, that may separately serve as information by which the perturbation can be identified in test samples.

Algorithm

The table below comprises some steps of the method according to an example of the invention in more detail. Herein data with a star relates to centered data (for instance $X_{i_{reference}}^*$, $X_{i_{perturbed}}^*$ and $X_{i_{test}}^*$) and the process of centering is referred to as pre-processing.

| Step # | | Explanation | Calculation |
|---|---|---|---|
| 1 | | Pre-process reference surface marker-profiles | $X_{i_{reference}}^* = S_{control}^{-1}(X_{i_{reference}} - 1_{N_{i_{reference}}} m_{i_{reference}}^T)$ |
| 2 | a | Construct control PCA model, on object count weighted sample data | $N_{i_{reference}}^{-2} X_{i_{reference}}^* = T_{control,i_{reference}} P_{control}^T$ <br> Under the constraint <br> $P_{control}^T P_{control} = I$ |
| | b | re-weight control scores | $T_{control,i_{reference}}^* = N_{i_{reference}}^2 T_{control,i_{reference}}$ |
| 3 | | determine control residuals | $Y_{i_{healthly}} = X_{i_{reference}}^* - T_{control,i_{reference}}^* P_{control}^T$ |
| 4 | | pre-process perturbed surface marker-profiles | $X_{i_{perturbed}}^* = S_{control}^{-1}(X_{i_{perturbed}} - 1_{N_{i_{perturbed}}} m_{i_{perturbed}}^T)$ |

-continued

| Step # | Explanation | Calculation |
|---|---|---|
| 5 | project perturbed surface marker-profiles on control loadings | $T_{TC,i_{perturbed}} = X_{i_{perturbed}} * P_{control}$ |
| 6 | Determine residuals of the projection | $Y_{i_{perturbed}} = X_{i_{perturbed}} * - T_{TC,i_{perturbed}} P_{control}^T$ |
| 7 a | Construct perturbation PCA model | $N_{i_{perturbed}}^{-2} Y_{i_{perturbed}} = T_{perturbation,i_{perturbed}} P_{perturbation}^T$ |
| | | Under the constraint |
| b | re-weight perturbation scores | $P_{perturbation}^T P_{perturbation} = I$ $T_{perturbation,i_{perturbed}} * = N_{i_{perturbed}}^2 T_{perturbation i_{perturbed}}$ |
| 8 | Project reference surface marker-profiles on the perturbation loadings | $T_{CT,i_{reference}} = X_{i_{reference}} * P_{perturbation}$ |
| 9 | Pre-process data from a 'test' sample with unknown health status | $X_{i_{test}}^* = S_{control}^{-1}(X_{i_{test}} - 1_{N_{i_{test}}} m_{i_{test}}^T)$ |
| 10 | Project pre-processed 'test' data onto the control loadings | $T_{CT,i_{test}} = X_{i_{test}} * P_{control}$ |
| 11 | Project pre-processed 'test' data on the perturbation loadings | $T_{CT,i_{test}} = X_{i_{test}} * P_{perturbation}$ |

The method may be executed using a computer running software. The computer can receive the data via one or more I/O ports and send the results of the method via one or more further I/O ports.

In a second example of the computer implemented method according to the invention, the confidence level of the confidence intervals is determined automatically. The inventors realised that a perturbed sample of objects in the second set of data may comprise objects that could have been found in a reference sample and objects that could not be found in a reference sample as they correspond specifically to the perturbation. Correspondingly, the measured values of such samples may differ within the second set of data.

According to the example, the confidence level of the confidence interval that is determined using the perturbation scores $T_{perturbation,i_{perturbed}}*$ of each perturbed sample is incrementally varied between for instance 50% and 100% in steps of 1 percent in an incremental cycle and at the same time the confidence level of the confidence interval that is determined using the scores $T_{CT,i_{reference}}$ of all reference samples is incrementally varied with the same value. By increasing the confidence level, a different number of objects and thus samples in the second set of data will be classified as differing from the reference data. The average percentage of objects of each perturbed individual that score outside the confidence interval divided by the average number of scores $T_{CT,i_{reference}}$ that score outside this same confidence interval is a measure of the diagnostic ability of the method. The confidence level of the confidence interval may be established at the level where the value of this diagnostic ability is highest. While incrementing the confidence level, the diagnostic ability is determined with a computer. The corresponding confidence level is selected and the corresponding confidence interval is used when feeding the test data into the method to diagnose samples with improved reliability and in a more quantifiable way. The same sensitivity analysis may be used for the determination of diagnostic ability of the reference model, by varying the confidence level of the confidence interval on perturbation scores $T_{TC,i_{perturbed}}$ with the same confidence level on $T_{control,i_{reference}}*$.

This also allows the calculation of a diagnostic ability, for which the highest level may be selected at the confidence level of the confidence interval. The diagnostic ability may also be calculated based on Analysis of Variance or another statistical test to compare values from two or more groups of samples.

This selected confidence level is used to process the test set of data according to the method as described earlier.

The method of this example provides a more reliable and quantifiable diagnosis.

In a third example of the invention, the computer implemented method for the first example is implemented on the cytometer which is provided with a sorter.

The sorter selects objects from the perturbed samples. The selection $N_{i_{perturbed}}^{\#}$ comprises both:

objects that score outside the confidence interval based on the complete first data set; and objects that score with the confidence interval based on the complete first data set and have a value in the matrix $Y_{i_{perturbed}}$ that exceeds a threshold, wherein the threshold is determined based on residual values observed for the reference samples.

The data of the selected objects is used to fit a further perturbation model, i.e. is forms a further second set of data that is processed instead of the second set of data.

This kind of selection is advantageous in early stages of scientific research to determine important aspects to be studied and to improve the method as it delivers a set of objects that differs in a well-defined way from the objects in the reference samples.

Clauses

The invention can be summarized by the following set of clauses.

1 Method of analysing data comprising measured values of characteristics of objects in samples, the data comprising
    a first set of data ($X_{i_{reference}}$) with measured values of characteristics of objects in reference samples;
    a test set of data ($X_{i_{test}}$) with measured values of the characteristics of objects in a test sample;

characterised by the method comprising;
fitting a control model to the first set of data to determine control loadings ($P_{control}$) each representing an independent correlation between characteristics;
projecting the first set of data ($X_{i_{reference}}$) onto the control loadings ($P_{control}$) for determining a first set control scores ($T_{control,i_{reference}}$) and determining one or more confidence intervals for the first set of control scores ($T_{control,i_{reference}}$);
projecting the test data onto the control loadings ($P_{control}$) for determining test control scores;
determining if the test control scores are within one or more the confidence intervals.

2 Method according to clause 1, wherein the step of fitting a control model comprises using a principal component analysis to determine the control loadings ($P_{control}$).

3 Method according to clause 1 or 2, wherein the first set of data ($X_{i_{reference}}$) is centered per sample by determining per reference sample ($i_{inference}$) the mean value ($m_{i_{reference}}$) of each characteristic and subtracting for each reference sample ($i_{reference}$) the corresponding mean value ($m_{i_{reference}}$) of the characteristic from the measured value in the first set of data ($X_{i_{reference}}$) of the corresponding characteristic before fitting the control model.

4 Method according to clause 1, 2 or 3, wherein the test set of data ($X_{i_{test}}$) is centered per sample by determining per test sample ($i_{test}$) the mean value of each characteristic and subtracting for each test sample ($i_{test}$) the corresponding mean value of the characteristic from the measured value in the test set of data of the corresponding characteristic before projecting the test data onto the control loadings ($P_{control}$).

5 Method according to any of the clauses 1, 3 or 4 and claim 2, comprising
using the principal component analysis to select two principal control loadings ($P_{control}$)
producing a biplot of the test control scores, the biplot comprising a vector corresponding to a characteristic of the objects of the data;
determining if the test control scores along the vector are within the one or more confidence intervals.

6 Method according to any of the clauses 1 to 5, wherein a first set of control residuals ($Y_{i_{reference}}$) is determined by projecting the first set of data ($X_{i_{reference}}$) onto the control loadings ($P_{control}$), and
wherein a test set of control residuals is determined by projecting the test set of data onto the control loadings ($P_{control}$),
comprising
projecting a second set of data ($X_{i_{perturbed}}$) with measured values of the characteristics of objects in perturbed samples onto the control loadings ($P_{control}$) for determining a second set of control residuals ($Y_{i_{perturbed}}$);
fitting a perturbation model to the second set of control residuals ($Y_{i_{perturbed}}$) to determine perturbation loadings ($P_{perturbation}$) each representing an independent correlation between characteristics;
projecting the first set of control residuals ($Y_{i_{reference}}$) onto the perturbation loadings ($P_{perturbation}$) and determining a first set of perturbation scores ($T_{CT,i_{reference}}$);
determining one or more further confidence intervals for the first set of perturbation scores ($T_{CT,i_{reference}}$);
projecting the test data onto the control loadings ($P_{control}$) to determine test control residuals;
projecting the test control residuals onto the perturbation loadings ($P_{response}$) and determining a test perturbation scores;
comparing the test perturbation scores with the one or more further confidence intervals.

7 Method according to clause 6, wherein the step of fitting a perturbation model comprises using a principal component analysis to determine the perturbation loadings 8 Method according to clause 6 or 7, wherein the test set of data is the second set of data.

9 Method according to clause 8, comprising removing data corresponding to test scores falling within the one or more confidence intervals from the second set of data before fitting the perturbation model.

10 Method according to any of the clauses 8 or 9 comprising
projecting the second set of control residuals ($Y_{i_{perturbed}}$) onto the perturbation loadings to determine a second set of perturbation scores;
determining an additional confidence interval for the second set of perturbation scores.

11 Method according to clause 7 and according to clause 6, 8, 9 or 10, comprising
using the further principal component analysis to select two principal perturbation loadings ($P_{perturbation}$);
producing a biplot of the test perturbation scores, the biplot comprising a vector corresponding to a characteristic of the objects of the data;
determining if the test perturbation scores along the vector are within the one or more further confidence intervals.

12 Computer program comprising program code for performing the steps of any of the clauses 1 to 11 when said computer program is executed on a computer.

13 Computer readable medium comprising the computer program according to clause 11.

14 Data analysis system for analysing data comprising measured values of characteristics of objects in samples, comprising computation means arranged to carry out the steps of any of the clauses 1 to 11.

The invention claimed is:

1. A computer-implemented method of identifying objects in a test set of data, the method comprising:
collecting, from memory, a first set of data with measured values of characteristics of ten or more objects in reference samples and associated with individuals that are not subjected to a challenge or diseased, each of the reference samples taken from a unique individual;
collecting, from the memory, the test set of data with the measured values of the characteristics of ten or more objects in a test sample;
creating a control model using the first set of data, the control model including a plurality of control loadings, each of the control loadings representing an independent relationship between characteristics of the objects in the first set of data;
creating a first set of control scores based on the first set of data and the plurality of control loadings in the control model;
automatically determining one or more confidence intervals for the first set of control scores;
creating test control scores for the objects in the test set of data based on the measured values of the characteristics of the objects in the test sample and the plurality of control loadings in the control model;
determining if the test score values are within the one or more confidence intervals;
creating a first set of control residuals based on the control loadings and the first set of data;
creating a test set of control residuals based on the test set of data and the control loadings;

creating a second set of control residuals based on a second set of data with measured values of the characteristics of objects in perturbed samples and the control loadings;

creating perturbation loadings based on fitting a perturbation model to the second set of control residuals, wherein each of the perturbation loadings represents an independent correlation between characteristics;

creating a first set of perturbation scores based on the first set of control residuals and the perturbation loadings;

automatically determining one or more further confidence intervals for the first set of perturbation scores; and creating test control residuals based on the test set of data and the control loadings;

creating test perturbation scores based on the test control residuals and the perturbation loadings; and identifying objects in the test sample differing from the objects in the reference samples based on whether the test perturbation scores for the objects in the test set of data are outside the one or more further confidence intervals.

2. The computer implemented method of claim 1, wherein the objects are cells.

3. The computer implemented method of claim 1, wherein the objects are particles.

4. The computer implemented method of claim 1, further comprising: creating a biplot of the test control scores, the biplot comprising a vector corresponding to a characteristic of the objects of the data projected onto two principal control loadings of at least two principal control loadings; and determining if the test control scores along the vector are within the one or more confidence intervals.

5. The computer implemented method of claim 1, wherein the test set of data is the second set of data.

6. The computer implemented method of claim 1, further comprising removing data corresponding to test scores falling within the one or more confidence intervals from the second set of data before fitting the perturbation model to the second set of control residuals.

7. The computer implemented method of claim 1, further comprising:
creating a second set of perturbation scores based on the second set of control residuals and the perturbation loadings; and
determining an additional confidence interval for the second set of perturbation scores.

8. A method for analysing data comprising the steps of the computer implemented method according to claim 1; and
using a cytometer to measure the values of characteristics of the objects in the test sample.

9. A non-transitory computer readable medium having stored therein an information processing program for identifying objects in a test set of data, the information processing program when executed by a computer controls the computer to:
collect, from memory, a first set of data with measured values of characteristics of ten or more objects in reference samples and associated with individuals that are not subjected to a challenge or diseased, each of the reference samples taken from a unique individual;
collect, from the memory, the test set of data with the measured values of the characteristics of ten or more objects in a test sample;
create a control model using the first set of data, the control model including a plurality of control loadings, each of the control loadings representing an independent relationship between characteristics of the objects in the first set of data;
create a first set of control scores based on the first set of data and the plurality of control loadings in the control model;
automatically determine one or more confidence intervals for the first set of control scores;
create test control scores for the objects in the test set of data based on the measured values of the characteristics of the objects in the test sample and the plurality of control loadings in the control model;
determine if the test score values are within the one or more confidence intervals;
create a first set of control residuals based on the control loadings and the first set of data;
create a test set of control residuals based on the test set of data and the control loadings;
create a second set of control residuals based on a second set of data with measured values of the characteristics of objects in perturbed samples and the control loadings;
create perturbation loadings based on fitting a perturbation model to the second set of control residuals, wherein each of the perturbation loadings represents an independent correlation between characteristics;
create a first set of perturbation scores based on the first set of control residuals and the perturbation loadings;
automatically determine one or more further confidence intervals for the first set of perturbation scores; and
create test control residuals based on the test set of data and the control loadings;
create test perturbation scores based on the test control residuals and the perturbation loadings; and
identify objects in the test sample differing from the objects in the reference samples based on whether the test perturbation scores for the objects in the test set of data are outside the one or more further confidence intervals.

10. A cytometer for identifying objects in a test set of data, the cytometer comprising memory and a computer operably coupled to the memory, wherein the computer is configured to:
collect, from the memory, a first set of data with measured values of characteristics of ten or more objects in reference samples measured by the cytometer and associated with individuals that are not subjected to a challenge or diseased, each of the reference samples taken from a unique individual;
collect, from the memory, the test set of data with the measured values of the characteristics of ten or more objects in a test sample;
create a control model using the first set of data, the control model including a plurality of control loadings, each of the control loadings representing an independent relationship between characteristics of the objects in the first set of data;
create a first set of control scores based on the first set of data and the plurality of control loadings in the control model;
automatically determine one or more confidence intervals for the first set of control scores;
create test control scores for the objects in the test set of data based on the measured values of the characteristics of the objects in the test sample and the plurality of control loadings in the control model;

determine if the test score values are within the one or more confidence intervals;

create a first set of control residuals based on the control loadings and the first set of data;

create a test set of control residuals based on the test set of data and the control loadings;

create a second set of control residuals based on a second set of data with measured values of the characteristics of objects in perturbed samples and the control loadings;

create perturbation loadings based on fitting a perturbation model to the second set of control residuals, wherein each of the perturbation loadings represents an independent correlation between characteristics;

create a first set of perturbation scores based on the first set of control residuals and the perturbation loadings;

automatically determine one or more further confidence intervals for the first set of perturbation scores; and create test control residuals based on the test set of data and the control loadings;

create test perturbation scores based on the test control residuals and the perturbation loadings; and identify the objects in the test sample differing from the objects in the reference samples based on whether the test perturbation scores for the objects in the test set of data are outside the one or more further confidence intervals.

11. The cytometer according to claim 10, further comprising a gating device for selecting objects, the gating device configured to separate the objects of the test sample based on corresponding test control scores and check if the corresponding test control scores are inside the one or more confidence intervals.

12. The cytometer according to claim 10, wherein the computer is further configured to:

display, on a display, a biplot of the test control scores, the biplot comprising a vector corresponding to a characteristic of the objects of the data projected onto two principal control loadings of at least two principal control loadings.

13. The cytometer according to claim 12, wherein the computer is further configured to automatically determine if the test control scores along the vector are within the one or more confidence intervals.

14. The cytometer according to claim 10, wherein the cytometer is a flow cytometer or a mass cytometer.

15. The cytometer according to claim 10, further comprising a display, and wherein the computer is further controlled to: control the display to output a graphical representation of the test perturbation scores related to the test set of data.

* * * * *